United States Patent [19]

Cook, Jr.

[11] 4,273,725

[45] Jun. 16, 1981

[54] PROCESS FOR PREPARING CHLOROTHIOLFORMATES

[75] Inventor: James A. Cook, Jr., Barberton, Ohio

[73] Assignee: PPG Industries, Inc., Pittsburgh, Pa.

[21] Appl. No.: 60,319

[22] Filed: Jul. 25, 1979

[51] Int. Cl.$^3$ .................... C07C 153/01; C07B 29/00; C07C 51/58

[52] U.S. Cl. ................ 260/455 R; 260/691; 260/544 K

[58] Field of Search ................ 260/455 R, 691, 544 K

[56] References Cited

U.S. PATENT DOCUMENTS

| | | | |
|---|---|---|---|
| 2,170,262 | 8/1939 | Graenacher et al. | 260/691 |
| 2,251,695 | 8/1941 | Tucker | 260/691 |
| 2,913,327 | 11/1959 | Tilles | 260/455 A |
| 3,093,537 | 6/1963 | Tilles | 260/455 A |
| 3,126,406 | 3/1964 | Tilles | 260/455 A |
| 3,165,544 | 1/1965 | Tilles | 260/455 A |
| 3,175,897 | 3/1965 | Tilles | 260/455 A |
| 3,185,720 | 5/1965 | Tilles | 260/455 A |
| 3,299,114 | 1/1967 | Tilles | 260/455 A |
| 3,896,169 | 7/1975 | Tilles et al. | 260/455 A |
| 4,012,405 | 3/1977 | Alesandrini | 260/455 A |
| 4,119,659 | 10/1978 | Alesandrini | 260/455 A |

OTHER PUBLICATIONS

Beckwith, A. L. J., The Chem. of Amides, Interscience Publishers, John Wiley & Sons, 1970.
Kirk-Othmer, Encyclopedia of Chemical Technology, 2nd Ed., vol. 16, pp. 841, 842, 850.
Morrison & Boyd, Organic Chemistry, pp. 834-842.
Acheson, Intro. to the Chem. of Heterocyclic Compounds, 2nd Ed., pp. 62-70.
H. K. Hall, Jr., J. Chem. Phys., vol. 60, pp. 63-70 (1956).

*Primary Examiner*—Henry R. Jiles
*Assistant Examiner*—Robert C. Whittenbaugh
*Attorney, Agent, or Firm*—Irwin M. Stein

[57] ABSTRACT

Chlorothiolformates are prepared by reacting a mercaptan with phosgene in the presence of a catalyst selected from a group consisting of (1) secondary amine and (2) secondary amine hydrochloride.

21 Claims, No Drawings

PROCESS FOR PREPARING CHLOROTHIOLFORMATES

DESCRIPTION OF THE INVENTION

The catalytic preparation of alkyl and phenyl chlorothiolformates by reaction of the appropriate mercaptan, e.g., an alkyl or phenyl mercaptan, with phosgene has been described in the patent literature. In the absence of catalyst, the reaction can require several days to achieve substantially complete reaction. Exemplary of U.S. patents directed to the preparation of chlorothiolformates are U.S. Pat. Nos. 3,165,544, 3,093,537, 4,012,405 and 4,119,659, which describe the use of activated carbon for the preparation of alkyl and phenyl chlorothiolformates, and U.S. Pat. No. 3,299,114, which describes the use of tertiary amines and heterocyclic amine compounds to catalyze the aforesaid reaction.

It has now been discovered that secondary amines and secondary amine hydrochlorides can be used to catalyze the reaction of mercaptan with phosgene. In particular, the secondary amine can be represented by the general formula, $R_1R_2NH$, wherein $R_1$ and $R_2$ are each selected from the group consisting of alkyl, alkenyl, cycloalkyl, cycloalkylmethyl, lower alkyl substituted cycloalkyl, aryl, halo-substituted aryl, lower alkyl substituted aryl, aralkyl and halo-substituted aralkyl. The secondary amine hydrochloride can be represented by the general formula, $R_1R_2NH.HCl$, wherein $R_1$ and $R_2$ are the same as hereinbefore defined.

DETAILED DESCRIPTION OF THE INVENTION

The present invention relates to the use of a secondary amine or secondary amine hydrochloride as a catalyst for the reaction of a mercaptan with phosgene to produce chlorothiolformates. The reaction can be represented by the following balanced equation:

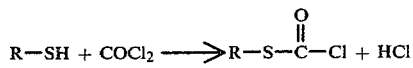

(1)

Certain chlorothiolformates, e.g. ethyl chlorothiolformate, have been found useful as pesticides. See for example U.S. Pat. No. 3,093,537. In addition, chlorothiolformates, e.g., ethyl chlorothiolformate, have been found useful as intermediates for the preparation of herbicidally effective thiolcarbamates and similar compounds. See, for example, U.S. Pat. Nos. 2,913,327, 3,126,406, 3,175,897 and 3,185,720. In the latter patents, thiolcarbamates are reacted further with amines to produce the corresponding thiolcarbamate.

The use of secondary amines as catalysts for the reaction of mercaptan with phosgene has the added benefit of not requiring separation of the catalyst from the chlorothiolformate when it is used as an intermediate for the preparation of thiolcarbamates for the reason that secondary amines are used typically as a reactant in the thiolcarbamate forming reaction. Thus, an appropriate secondary amine can be selected for use as the catalyst in the process described herein and any amine present in the chlorothiolformate product will serve as a reactant in the subsequent thiolcarbamate forming reaction, thereby avoiding the introduction of by-product impurities in the thiolcarbamate product.

Secondary amine compounds useful as catalysts for the reaction of mercaptans with phosgene are secondary amines and secondary amine hydrochlorides having the general formulae, $R_1R_2NH$ and $R_1R_2NH.HCl$, wherein $R_1$ and $R_2$ are each selected from the group consisting of $C_1$–$C_{12}$ alkyl, $C_3$–$C_4$ alkenyl, $C_3$–$C_6$ cycloalkyl, $C_3$–$C_6$ cycloalkylmethyl, lower alkyl substituted $C_3$–$C_6$ cycloalkyl, $C_6$–$C_{10}$ aryl, halo-substituted $C_6$–$C_{10}$ aryl, lower alkyl substituted $C_6$–$C_{10}$ aryl, $C_6$–$C_{10}$ aralkyl and halo-substituted $C_6$–$C_{10}$ aralkyl. As used in the specification and claims, the term "lower alkyl" is intended to mean and include alkyl groups having from 1 to 4 carbon atoms ($C_1$–$C_4$ alkyl); and, the prefix "halo" is intended to mean and include a halogen substituent, e.g., chloro, bromo, fluoro and iodo, preferably chloro or bromo, on the aromatic ring. Preferred secondary amine and secondary amine hydrochlorides are those wherein $R_1$ and $R_2$ are each selected from the group $C_1$–$C_6$, more preferably $C_1$–$C_4$, alkyl and $C_3$–$C_6$ cycloalkyl. Moreover, as used hereinafter in the specification and claims, the term secondary amine is intended to include the corresponding secondary amine hydrochloride. The secondary amine compounds represented by the abovedescribed formulae can be prepared by methods well known in the art.

As further examples of secondary amines that are useful as catalysts for the process described herein, reference is made to U.S. Pat. Nos. 3,126,406 and 3,896,169 and particularly Table I of the latter patent. These patents describe thiolcarbamate compounds which contain the radical,

which, if a hydrogen atom were added to the nitrogen atom, denotes a variety of secondary amines. Such amines are exemplary of secondary amines that have been used in the art to prepare thiolcarbamates, and are exemplary of the secondary amine catalysts described by the aforesaid general formulae.

As examples of $C_1$–$C_{12}$ alkyl radicals, there can be mentioned methyl, ethyl, n-propyl, isopropyl, n-butyl, isobutyl, secondary butyl, tertiary butyl, n-pentyl, neopentyl, hexyl, neohexyl t-heptyl, n-octyl, 2-ethylhexyl, n-nonyl, n-decyl, and n-dodecyl. As examples of alkenyl radicals, there can be mentioned allyl, methallyl, and butenyl.

As examples of $C_3$–$C_6$ cycloalkyl, $C_3$–$C_6$ cycloalkylmethyl and lower alkyl substituted $C_3$–$C_6$ cycloalkyl radicals, there can be mentioned, cyclopropyl, cyclobutyl, cyclopentyl, cyclohexyl, 3-methyl cyclohexyl, dimethyl cyclohexyl, 1-methyl cyclopropyl, 3-methyl cyclobutyl, 2-ethyl cyclopropyl, cyclopropylmethyl, cyclopentylmethyl, cyclobutylmethyl, 1-methyl cyclopropylmethyl, 3-methyl cyclopentylmethyl, 3-methylcyclobutylmethyl and 2-ethyl cyclopropylmethyl.

Among the aryl, mono- and dihalo-substituted aryl, lower alkyl substituted aryl, aralkyl, and halo-substituted aralkyl radicals, there can be mentioned phenyl, 4-chlorophenyl, 2-tolyl, 3-tolyl, 2-naphthyl, 3-chloro-4-methyl phenyl, 4-bromophenyl, benzyl, 4-chlorobenzyl and 2-phenylethyl.

The amount of secondary amine catalyst used to catalyze the reaction of the mercaptan with phosgene is that amount which is required to accelerate the reaction to commercially acceptable rates, i.e., a catalytic amount. Whereas several days may be required to accomplish significant conversions of mercaptan, e.g., greater than 80 percent conversion, in the absence of catalyst, such conversions can be accomplished within 4 to 16 hours with use of a secondary amine catalyst. Typically, between about 0.01 and about 10 mole percent of secondary amine, based on the mercaptan, can be used. More commonly, between about 0.05 and about 0.5 or 1 mole percent of secondary amine catalyst is used. It has been found, for example, that between 0.01 and 0.05 mole percent of di-n-propyl amine, based on mercaptan, catalyzes the reaction of ethyl or n-propyl mercaptan with phosgene at economical rates and yields the corresponding chlorothiolformate of high quality.

The secondary amine catalyst can be added to the reactor separately, dissolved in the phosgene or mixed with the mercaptan. In a preferred embodiment, the amine catalyst is added slowly to a pool of phosgene or added slowly to the phosgene admixed with the mercaptan during the initial stages of the reaction rather than being added all at once.

Mercaptans that can be reacted with phosgene in the presence of secondary amine catalyst can be represented by the formula, R—SH, wherein R is alkyl, cycloalkyl, cycloalkylmethyl, lower alkenyl, aryl, alkaryl, aralkyl, haloaryl, haloaralkyl, and carboalkoxy alkyl. Such mercaptans are well recognized in the art, as can be seen by reference to the aforesaid described U.S. patents. Mercaptans, such as those described herein, can be prepared by methods known in the art. Among the methods described in the art for preparing mercaptans are the reaction of an alkali alkyl sulfate or alkyl halide with sodium or potassium hydrosulfide; the vapor phase reaction of the appropriate alcohol with hydrogen sulfide; and the addition of hydrogen sulfide to the appropriate unsaturated organic compound.

Typically, R in the formula R—SH is a branched or straight chain $C_1$–$C_{15}$ alkyl, $C_2$–$C_5$ alkenyl, $C_3$–$C_7$ cycloalkyl or cycloalkylmethyl, $C_6$–$C_{10}$ aryl, $C_6$–$C_{10}$ alkaryl or aralkyl, and $C_6$–$C_{10}$ haloaryl or haloaralkyl and $C_2$–$C_{10}$ carboalkoxyalkyl. The halo prefix includes the halogen substituents, i.e., chloro, bromo, fluoro and iodo, preferably chloro and bromo. Generally the aliphatic and aromatic radicals described with respect to the secondary amine are also suitable as substituents for the R group of the mercaptan. More typically, R is a $C_1$–$C_{10}$, preferably $C_1$–$C_6$ alkyl, $C_3$–$C_4$ alkenyl, $C_5$–$C_6$ cycloalkyl or cycloalkylmethyl, phenyl, $C_1$–$C_4$ alkyl substituted phenyl, chlorophenyl including mono- and polychlorinated phenyl, benzyl and chlorobenzyl, including mono- and polychlorinated benzyl, and $C_2$–$C_5$ carboalkoxyalkyl.

Examples of organic mercaptans which can be suitably used in the reaction of the present invention are alkyl mercaptans such as methylmercaptan, ethylmercaptan, isopropylmercaptan, n-propylmercaptan, isobutylmercaptan, secondary butylmercaptan, n-butylmercaptan, 2-pentylmercaptan, neopentylmercaptan, n-pentylmercaptan, n-hexylmercaptan, neohexylmercaptan, n-heptylmercaptan, n-octylmercaptan, and the like. As examples of cycloalkyl mercaptans, the following can be employed: cyclopentylmercaptan, cyclohexylmercaptan, 2-methylcyclohexylmercaptan, 3-methylcyclohexylmercaptan, cyclopropylmethylmercaptan, cyclopentylmethylmercaptan, cyclohexylmethylmercaptan, and the like. Allyl mercaptan and butenyl mercaptan are typical examples of lower alkenyl mercaptans that can be used in the above defined reaction.

Also useful are aryl, alkaryl, aralkyl, haloaryl and haloaralkyl compounds exemplified by the following compounds: mercaptobenzene, 2-mercaptonaphthalene, 4-mercaptotoluene, 2-mercaptotoluene, 3-mercaptotoluene, 2,4-dimethylmercaptobenzene, 2,5-dimethylmercaptobenzene, 4-tert-butylmercaptobenzene, 1-methyl-2-mercaptonaphthalene, 4-ethylmercaptobenzene, benzylmercaptan, mercaptoethyl benzene, mercaptopropyl benzene, triphenylmethyl mercaptan, mercaptomethyl naphthalene, mercaptoethyl naphthalene, mercaptobutyl naphthalene, 2-chloromercaptobenzene, 3-chloromercaptobenzene, 4-chloromercaptobenzene, 2,5-dichloromercaptobenzene, 4-bromomercaptobenzene, 2-iodomercaptobenzene, 3-iodomercaptobenzene, 4-iodomercaptobenzene, 2-chlorobenzylmercaptan, 3-chlorobenzylmercaptan, 4-chlorobenzylmercaptan, 2,4-dichlorobenzylmercaptan, 3,4-dichlorobenzylmercaptan, 4-bromobenzylmercaptan, 4-chloro-1-mercaptonaphthalene, 4-bromo-1-mercaptonaphthalene, and the like. Similarly, examples of carboalkoxyalkyl mercaptans that can be reacted with phosgene according to the present invention are those compounds typified as esters of mercapto-acids. Suitable examples are methyl mercaptoacetate, ethyl mercaptoacetate, propyl mercaptoacetate, butyl mercaptoacetate, pentyl mercaptoacetate, hexyl mercaptoacetate, methyl 2-mercaptopropionate, ethyl 2-mercaptopropionate, pentyl 2-mercaptopropionate, methyl 3-mercaptopropionate, ethyl 3-mercaptopropionate, hexyl 3-mercaptopropionate, methyl 2-mercaptobutyrate, propyl 2-mercaptobutyrate, hexyl 2-mercaptobutyrate, methyl 3-mercaptobutyrate, ethyl 3-mercaptobutyrate, hexyl 3-mercaptobutyrate, methyl 4-mercaptobutyrate, ethyl 4-mercaptobutyrate, hexyl 4-mercaptobutyrate, methyl 3-mercaptovalerate, ethyl 3-mercaptovalerate, hexyl 3-mercaptovalerate, methyl 5-mercaptovalerate, ethyl 5-mercaptovalerate, hexyl 5-mercaptovalerate, and the like.

The amount of phosgene used in the reaction can vary; but is typically at least a stoichiometric amount based on equation (1). That is, at least one mole of phosgene is used for every mole of mercaptan. More usually, an excess of phosgene, e.g., from about 5 to about 50 mole percent excess phosgene, based on the mercaptan is used for the reasons that the phosgene can be removed readily from the reaction mixture and an excess of mercaptan will favor the production of by-product dithiolcarbonate.

Reaction of the mercaptan with phosgene is commonly conducted at atmospheric pressure, although subatmospheric or superatmospheric pressures can be used. Reaction temperatures should be maintained as low as possible, consonant with reasonable reaction rates since, at high temperatures, the dithiolcarbamate can be formed in significant amounts. Since the mercaptans described hereinbefore exhibit varying reactivities and varying decomposition temperatures such factors must be taken into account in selecting the reaction temperature. With an excess of phosgene, the reaction temperature will typically range between about 0° C. and about 70° C. at atmospheric pressure and with refluxing phosgene. More typically, reaction temperatures will range between about 10° C. and about 50° C., e.g., between 10° C. and 35° C.

The reactants can be introduced into a suitable reactor in any order or simultaneously; however, it is preferable to add the mercaptan to a pool of phosgene. Further, when carrying out the process on a batch basis, it is preferred that the mercaptan be added slowly to the pool of phosgene so as to control the heat of reaction and minimize the formation of by-product dithiolcarbonate. When phosgene is added to a pool of mercaptan, the reaction commences at a higher temperature than when the order of reactant introduction is reversed, thereby increasing the opportunity for formation of by-product dithiolcarbonate. Preferably, the secondary amine catalyst is added mixed with the mercaptan; however, it can be added to the pool of phosgene.

The reaction can be conducted batch-wise also by introducing the reactants to a heel of the chlorothiolformate, i.e., a portion of the reaction product of a previous preparation. Although the initial reaction temperature is higher than when mercaptan is added to a pool of phosgene, reaction times are shorter. Preparation of the chlorothiolformate by a continuous reaction is also contemplated.

The chlorothiolformate product prepared in accordance with the present process contains low levels of organic disulfide, i.e., R—S—S—R, and dithiolcarbonate by-products. The low level of disulfide impurity is in contrast to the significant quantities of such impurity that is found in chlorothiolformate prepared using activated carbon as the catalyst. See, for example, U.S. Pat. No. 4,012,405 (column 1) wherein from 3 to 7 percent of diethyl disulfide is produced during preparation of ethyl chlorothiolformate by reaction of ethyl mercaptan with phosgene in the presence of activated carbon catalyst. Further, the secondaryamine catalyst of the present process does not appear to catalyze the reaction of the chlorothiolformate with further mercaptan to produce the dithiolcarbonate by-product.

In conducting the reaction of the present process, the reaction mixture is usually agitated to assist in removing heat from the reactor. At the end of the reaction, excess phosgene is removed, e.g., by stripping. Phosgene can be stripped from the chlorothiolformate product by pulling a vacuum on the system—thereby permitting the phosgene to boil off; passing an inert gas, e.g., nitrogen, through the reaction mixture; or, heating the reaction mixture slightly to boil off the excess phosgene. Upon removal of the excess phosgene, the secondary amine catalyst, e.g., probably as the hydrochloride, will precipitate and can be removed from the chlorothiolformate by filtration. If the chlorothiolformate is to be converted to a thiolcarbamate by reaction with further secondary amine, either the same or a different amine from the secondary amine catalyst, residual amine catalyst need not be removed from the chlorothiolformate before its further reaction with the appropriate further amine reactant.

The degassed chlorothiolformate product is obtained in sufficient purity to be used in some commercial applications, e.g., as an intermediate for the preparation of thiolcarbamates. If further purification is desired, the chlorothiolformates can be distilled or recrystallized from a suitable solvent to obtain a more pure product.

In a typical embodiment of a batch process, about 0.6 mole of phosgene per mole of mercaptan used is condensed in a reactor to establish a pool of phosgene at about 10° C. Thereafter, the ethyl mercaptan containing about 0.5 mole percent of di-n-propyl amine (based on mercaptan) is introduced slowly into the reactor simultaneously with the further addition of about 0.6 mole of phosgene per mole of mercaptan used. The additional phosgene and mercaptan reactant are added to the reactor over a period of about one hour and the reaction maintained under constant agitation. Vaporized phosgene is condensed in a reflux condenser connected to the reactor and condensed phosgene returned to the reactor. As the reaction takes place, the phosgene and ethyl mercaptan are consumed and the boiling point of the reaction mixture rises from about 10° C. to about 27° C. at the end of the reaction. At the end of about 5-6 hours, excess phosgene and unreacted ethyl mercaptan are stripped from the reactor by degassing, and the chlorothiolformate product removed from the reactor.

While the above embodiment has been exemplified by ethyl mercaptan and di-n-propyl amine, other of the above described mercaptans or secondary amines can be substituted for the ethyl mercaptan and di-n-propyl amine respectively of the exemplification and expect to obtain the corresponding chlorothiolformate.

The present invention is more particularly described in the following examples which are intended as illustrative only since numerous modifications and variations therein will be apparent to those skilled in the art. In the examples, the purity of the chlorothiolformate product is reported as peak area percent, i.e., by estimating the area under the peaks of the chart produced by gas liquid chromatographic analysis.

EXAMPLE I

Phosgene (0.194 mole) was condensed into a 30 ml. serum bottle which was capped with a Viton septum. Ethyl mercaptan (0.171 mole) containing 0.01 mole of di-n-propylamine was then injected into the bottle by means of a syringe and hypodermic needle. The reaction mixture was stirred and allowed to warm from −70° C. to wet ice temperature (0° C.) and maintained there for 250 minutes. The reaction was followed by means of gas liquid chromatographic analysis (GLC) of the unreacted ethyl mercaptan. During the aforesaid period at 0° C., the reaction mixture was homogeneous and about 90 percent of the ethyl mercaptan reacted.

The reaction mixture was permitted to warm to room temperature overnight to remove excess phosgene. The crude product was washed two times with 30 ml. of distilled water to remove the amine catalyst, dried with sodium sulfate and recovered by filtration. 13.7 grams of a water white product, which was identified by GLC as ethyl chlorothiolformate of about 90 to 95 percent purity, was recovered. This represented a 64.3 percent yield based on the theoretical conversion of all ethyl mercaptan to ethyl chlorothiolformate.

EXAMPLE II

Phosgene (4.8 moles) was condensed into a one liter, round bottom, three-neck flask. The flask was equipped with a stirrer and motor, thermometer, addition funnel, phosgene inlet tube and a dry ice-acetone condenser and cooled with a wet ice bath. A mixture of 4.0 moles of ethyl mercaptan and 0.2 moles of di-n-propylamine was placed in the addition funnel. When approximately one-half of the phosgene was condensed into the reaction flask, the addition thereto of the ethyl mercaptan-di-n-propylamine mixture was started at a rate of 2–3 cc./minute with stirring. The temperature of the phosgene in the reaction flask at the start of ethyl mercaptan addition was 7° C. The ice bath was not used during the addition of the ethyl mercaptan, which took 117 minutes. The temperature of the reaction mixture at the end of the addition of ethyl mercaptan was 7.5° C.

The reaction mixture was stirred overnight (about 17½ hours) and a GLC analysis the next morning showed that most of the ethyl mercaptan had reacted. Excess phosgene and unreacted ethyl mercaptan were then removed from the reaction mixture by degassing with nitrogen at the end of the degassing step, a white solid separated from the reaction mixture and was removed from the flask by filtration. The reaction product was identified by GLC as ethyl chlorothiolformate of about 97.7 percent purity. It was estimated that the ethyl chlorothiolformate product contained about 0.05 percent each of diethyl disulfide (DEDS) and diethyl dithiolcarbonate (DETC). The yield of degassed product was calculated to be 84.2 percent, based upon a theoretical conversion of all ethyl mercaptan to ethyl chlorothiolformate. The white solid was identified by melting point determination to be di-n-propylamine hydrochloride.

EXAMPLE III

The procedure of Example II was repeated except that no di-n-propylamine was added to the ethyl mercaptan, and the ethyl mercaptan was added to the flask over a period of 89 minutes. Other than the refluxing phosgene, no signs that a reaction was taking place were observed. The temperature of the reaction mixture remained at 15° C. for at least 6 hours, and 12 hours after the addition of the ethyl mercaptan, the temperature was found to be 13° C. The reaction mixture was left stirring overnight.

The next morning (about 24 hours after the start of the run) it was found that the dry ice-acetone coolant in the reflux condenser was depleted, which allowed phosgene to escape from the reaction system. The reaction temperature was found to be 19° C. A GLC analysis of the reaction mixture indicated that there was no longer an excess of phosgene and only about one quarter of the ethyl mercaptan had reacted at that time. 92 grams of additional phosgene was added to the reactor at that time with stirring. The temperature of the reaction mixture dropped to about 17° C. and was left stirring for the rest of that day. The reflux condenser was cooled with a 50 percent ethylene glycol solution which was circulated through a refrigeration unit. The next afternoon, the reaction temperature was found to be 24° C. and a GLC analysis of the reaction mixture indicated that about one-half of the ethyl mercaptan had reacted. The following afternoon the reaction temperature was found to be 26° C. and a GLC analysis of the reaction mixture indicated that about three-quarters of the ethyl mercaptan had reacted.

The next day (after four days of reaction) the reaction mixture was degassed with nitrogen. The yield of ethyl chlorothiolformate was calculated to be 71.7 percent. Its identity was confirmed by GLC analysis which indicated that the ethyl chlorothiolformate was about 99.5 percent pure and contained about 0.1 percent DEDS and about 0.3 percent DETC as by-products.

EXAMPLE IV

The procedure of Example II was repeated except that 0.001 moles of di-n-propylamine was used as the catalyst, and 2.0 moles of ethyl mercaptan and 2.4 moles of phosgene were used. The ethyl mercaptan-catalyst mixture was added over a period of 50 minutes. The reaction temperature increased slowly from 8° C. (at the start of ethyl mercaptan addition) to 24° C. over 9 hours indicating that significant reaction had taken place. The run was terminated at that time due to aspiration of sodium hydroxide from a scrubber in the reaction system into the reaction flask. A GLC analysis of the reaction mixture 6½ hours after the start of ethyl mercaptan addition indicated that about 50% of the ethyl mercaptan had reacted.

EXAMPLE V

The procedure of Example IV was repeated except that 2.0 moles of n-propyl mercaptan, 2.2 moles of phosgene and 0.1 mole percent (based on n-propyl mercaptan) of di-n-propylamine catalyst was used. The n-propyl mercaptan was added slowly to the reaction flask over 108 minutes and the reaction temperature rose slowly from 9° C. to 26° C. over 9 hours. A GLC analysis of the reaction mixture 7 hours after the start of n-propyl mercaptan addition indicated that about 84 percent of the mercaptan had reacted. About 12½ hours following the start of n-propyl mercaptan addition, the reaction mixture was heated to 35° C. and degassed with argon for about 10 hours. The yield of degassed product was calculated to be 93.9 percent, based on the theoretical conversion of all the n-propyl mercaptan to the chlorothiolformate. The propylchlorothiolformate (the identity of which was confirmed by GLC) was determined by GLC analysis to be about 99.2 percent pure and to contain about 0.2 percent di-n-propyl dithiolcarbonate and about 0.6 percent unknowns.

The data of Examples I–V show that secondary amines, such as di-n-propyl amine, serve as catalyst for the preparation of organic chlorothiolformates by the reaction of organic mercaptans, such as ethyl or n-propyl mercaptan, with phosgene.

Although the present process has been described with reference to specific details of certain embodiments thereof, it is not intended that such details should be regarded as limitations upon the scope of the invention except as and to the extent that they are included in the accompanying claims.

I claim:

1. In the process of preparing organic chlorothiolformates by reacting an organic mercaptan having the formula,

R—SH with phosgene, the improvement which comprises conducting said reaction in the presence of a catalytic amount of a secondary amine catalyst having the formula,

$R_1R_2NH$ or $R_1R_2NH \cdot HCl$ wherein R is alkyl, cycloalkyl, cycloalkylmethyl, lower alkenyl, aryl, alkaryl, aralkyl, haloaryl, haloarylalkyl and carboalkoxyalkyl, and $R_1$ and $R_2$ are each selected from the group consisting of $C_1$–$C_{12}$ alkyl, $C_3$–$C_4$ alkenyl, $C_3$–$C_6$ cycloalkyl, $C_3$–$C_6$ cycloalkylmethyl, lower alkyl substituted $C_3$–$C_6$ cycloalkyl, $C_6$–$C_{10}$ aryl, halo-substituted $C_6$–$C_{10}$ aryl, lower alkyl substituted $C_6$–$C_{10}$ aryl, $C_6$–$C_{10}$ aralkyl and halo-substituted $C_6$–$C_{10}$ aralkyl.

2. The process of claim 1 wherein from 0.01 to 10 mole percent of secondary amine catalyst, based on the mercaptan, is used.

3. The process of claim 2 wherein from 0.05 to 1 mole percent of secondary amine catalyst is used.

4. The process of claims 1 wherein the secondary amine catalyst is selected from the group consisting of (1) secondary amine having the formula $R_1R_2NH$, wherein $R_1$ and $R_2$ are each selected from the group consisting of $C_1$–$C_{14}$ alkyl, cyclohexyl and allyl and (2) $R_1R_2NH \cdot HCl$, wherein $R_1$ and $R_2$ are the same as herein defined.

5. The process of claim 1 wherein R is a $C_1$–$C_{15}$ alkyl, $C_2$–$C_5$ alkenyl, $C_3$–$C_7$ cycloalkyl, $C_3$–$C_7$ cycloalkylmethyl, $C_6$–$C_{10}$ aryl, $C_{6-10}$ alkaryl, $C_6$–$C_{10}$ aralkyl, $C_6$–$C_{10}$ haloaryl, $C_6$–$C_{10}$ haloaralkyl or $C_2$–$C_{10}$ carboalkoxyalkyl.

6. The process of claims 1, 4 or 5 wherein from 0.01 to 10 mole percent of secondary amine catalyst, based on mercaptan, is used.

7. The process of claim 6 wherein from about 5 to about 50 mole percent excess phosgene is used.

8. The process of claim 6 wherein the reaction is conducted by adding the mercaptan slowly to a pool of phosgene.

9. The process of claim 6 wherein the catalyst is diethylamine, di-n-propylamine, di-n-butylamine, di-isobutylamine, ethyl cyclohexylamine, or di-allylamine.

10. In the process of preparing alkylthiolformates by reacting an alkyl mercaptan having the formula R—SH, wherein R is a $C_1$–$C_6$ alkyl, with phosgene, the improvement which comprises conducting said reaction in the presence of a catalytic amount of a secondary amine catalyst selected from the group consisting of (1) secondary amine having the formula $R_1R_2NH$, wherein $R_1$ and $R_2$ are each selected from the group consisting of $C_1$–$C_{12}$ alkyl, $C_3$–$C_4$ alkenyl, $C_3$–$C_6$ cycloalkyl and lower alkyl substituted $C_3$–$C_6$ cycloalkyl and (2) secondary amine hydrochloride having the formula, $R_1R_2NH \cdot HCl$, wherein $R_1$ and $R_2$ are the same as herein defined.

11. The process of claim 10 wherein between 0.05 and 1 mole percent of secondary amine catalyst, based on the mercaptan is used.

12. The process of claim 10 or 11 wherein R is ethyl or propyl and $R_1$ and $R_2$ are each selected from the group consisting of $C_2$–$C_4$ alkyl, cyclohexyl and allyl.

13. The process of claim 10 or 11 wherein from about 5 to about 50 mole percent excess phosgene is used.

14. The process of claim 12 wherein from about 5 to about 50 mole percent excess phosgene is used.

15. The process of claim 13 wherein the reaction is conducted by adding the mercaptan slowly to a pool of phosgene.

16. The process of claim 14 wherein the secondary amine catalyst is mixed with the mercaptan.

17. The process of claim 11 wherein $R_1$ and $R_2$ are each selected from the group consisting of $C_2$–$C_4$ allyl, cyclohexyl and alkyl, from about 5 to about 50 mole percent of excess phosgene is used, and the mercaptan is added slowly to a pool of phosgene.

18. A process which comprises reacting an organic mercaptan having the formula, R—SH, wherein R is a $C_1$–$C_6$ alkyl, with phosgene, said phosgene being present in amounts of from about 5 to about 50 mole percent excess, in the presence of a catalytic amount of a secondary amine catalyst having the formula, $R_1R_2NH$ or $R_1R_2NH \cdot HCl$, wherein $R_1$ and $R_2$ are each selected from the group consisting of $C_1$–$C_4$ alkyl, cyclohexyl and allyl to thereby produce a reaction product comprising the corresponding alkyl chlorothiolformate, degassing the reaction product to remove excess phosgene, and adding further secondary amine of the formula, $R_1R_2NH$, wherein $R_1$ and $R_2$ are as defined herein, to the degassed reaction product in amounts sufficient to convert the alkyl chlorothiolformate to the corresponding alkyl thiolcarbamate.

19. The process of claim 18 wherein from 0.05 to 1 mole percent of secondary amine catalyst is used.

20. The process of claim 19 wherein R is ethyl or propyl and $R_1$ and $R_2$ are each selected from the group consisting of $C_2$–$C_4$ alkyl, cyclohexyl and allyl.

21. The process of claim 20 wherein the further secondary amine is selected from the group consisting of diethylamine, di-n-propylamine, di-n-butylamine, di-isobutylamine, ethyl cyclohexylamine, or di-allylamine.

* * * * *

UNITED STATES PATENT AND TRADEMARK OFFICE
CERTIFICATE OF CORRECTION

PATENT NO. : 4,273,725
DATED : June 16, 1981
INVENTOR(S) : James A. Cook, Jr.

It is certified that error appears in the above-identified patent and that said Letters Patent are hereby corrected as shown below:

Claim 4, column 9, line 5, "$C_1-C_{14}$" should be --$C_1-C_4$--.

Claim 5, column 9, line 11, "$C_{6-10}$" should be --$C_6-C_{10}$--.

Signed and Sealed this

First Day of September 1981

[SEAL]

Attest:

GERALD J. MOSSINGHOFF

Attesting Officer

Commissioner of Patents and Trademarks